Oct. 20, 1931. E. L. POLLARD ET AL Plant Pat. 4

THORNLESS YOUNG DEWBERRY

Filed Oct. 6, 1930

Discoverers.
Elmer L. Pollard.
Jubal E. Sherrill.
by
Lockwood & Lockwood,
Their Attorneys.

Patented Oct. 20, 1931

Plant Pat. 4

UNITED STATES PATENT OFFICE

ELMER L. POLLARD AND JUBAL E. SHERRILL, OF CHINO, CALIFORNIA

THORNLESS YOUNG DEWBERRY

Application filed October 6, 1930. Serial No. 486,558.

This discovery relates to a new fruit bearing plant of the Young dewberry variety, which plant was discovered as a sport that indicated an individual variation from the parent stock or vine in the notable respect that it was thornless.

This sport, after a further development, indicated that its individual thornless characteristic was a permanent feature of the plant and that through it an entirely new thornless variety of Young dewberry has been developed.

The original thornless sport or bud was discovered by us on a vine growing in a ten acre field of thorny berry vines that are commonly known as "Young dewberries" and which on the Pacific Coast are commonly known as "Youngberries".

As is well known, the vine of the Young dewberry as well as all other species of dewberries known to us, are quite thickly covered with sharp thorns that not only are on the vines but also in varied sizes extend along the fruit and leaf stems, so it is quite difficult to gather the berries without the pickers injuring their hands. The thorns not only cause painful wounds on the pickers' hands but also tear their clothing and generally impede their labor.

Knowing how generally beneficial it would be to have a thornless variety of Young dewberry we took special care to propagate this thornless vine and in its cultivation and development endeavored to make permanent its thornless feature, which we have succeeded in doing.

In this connection we furnished specimens in 1928 to George M. Darrow who, at that time was senior pomologist of the Bureau of Plant Industry in the U. S. Department of Agriculture, and who later wrote an article entitled "Thornless sports of the Young dewberry" that was published in the Journal of Heredity for December, 1929, pp. 567–569 in which he mentioned the identical mutation of the Young dewberry that was found by us in 1928 and furnished to him. Since that time we have been continuously cultivating this new thornless variety of berries and on a sufficiently large scale and for a length of time to justify and prove our claim that it is a new thornless variety.

The accompanying drawings illustrate the thornless character of the Young dewberry, in which.

The discovery of the new thornless dewberry and its care and propagation and general characteristics are more particularly described as follows:

The sport was discovered growing in a ten acre field of Young dewberries with the parent vines heavily covered with thorns, and the discovery was made in the summer of 1928 on plant Number 1 and row 27 in a plot of ground known as Hayden Field, that is located about one mile west of Chino, California.

This sport and the product thereof have been under our constant care, attention and cultivation since the above date and we have propagated it on an extensive scale with thousands of the thornless plants ready for distribution to the public, and in this extensive development this plant holds its thornless characteristic perfectly and is deemed to be an entirely new variety of dewberry that is thornless in every respect.

The plant is a very strong grower, trailing in habit and propagates from the tips of the vines and has a relatively heavy foliage. The fruit is very large, dark wine color, very little acid, few seeds, flavor much like the red raspberry, is very productive and seasons early.

Figure 1:
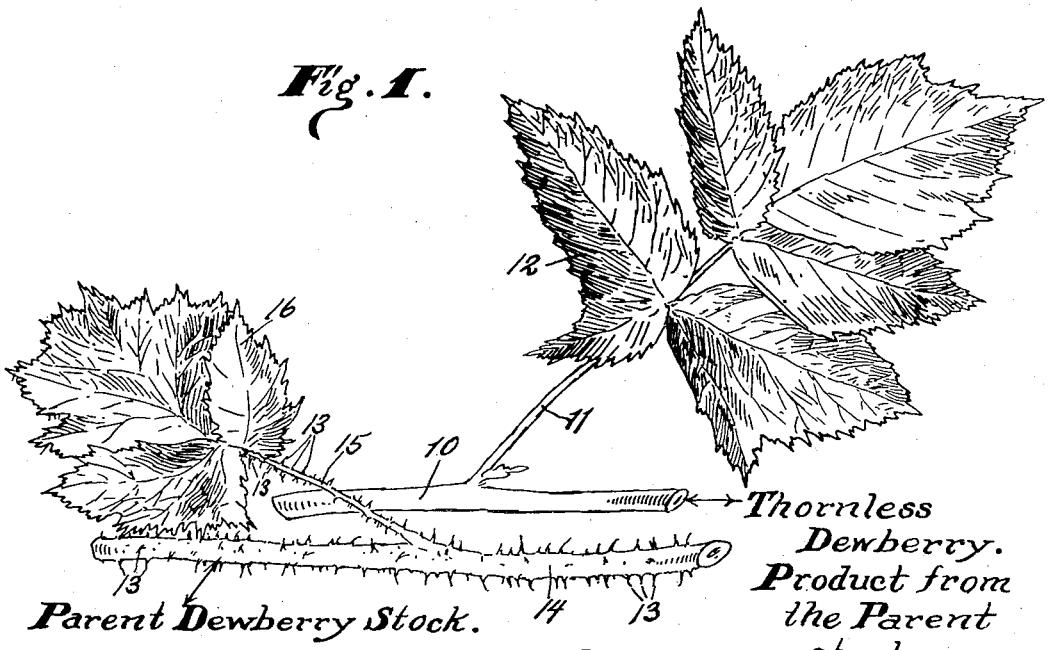
Fig. 1 is a grouped view of the parent thorny dewberry plant compared with its thornless product, also showing a comparison of the foliage.

In the drawings Fig. 1 shows our thornless dewberry arranged slightly above its parent plant and, as seen therein, its vine 10, stem 11 and leaf 12 are entirely free of the thorns 13 shown on the vine 14, stem 15 and leaf 16 of the parent stock.

Figure 2:
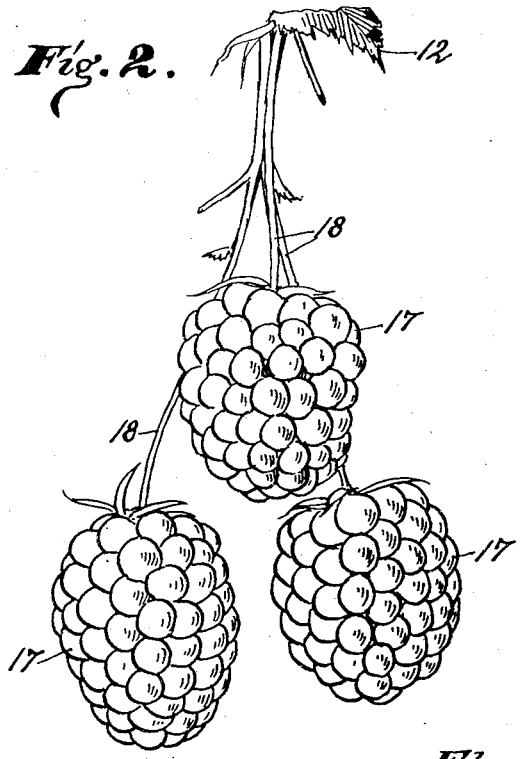
Fig. 2 is a view of a cluster of the thornless dewberry fruit with leaves and part of the fruit cluster cut away to better show three berries about actual size on their thornless stems.

In Fig. 2 a cluster of our thornless dewberry fruit is shown with part of the cluster and leaves cut away to more clearly show three of the berries 17 about actual size hanging on stems 18 that are thornless.

The color of the fruit is not shown, but is previously described as a dark wine color.

We claim:

A dewberry as herein shown and described characterized by the absence of thorns.

In witness whereof, we have hereunto affixed our signatures.

ELMER L. POLLARD.
JUBAL E. SHERRILL.